United States Patent [19]

Van Saun, Jr.

[11] 4,239,773
[45] Dec. 16, 1980

[54] INSECTICIDAL ESTERS OF CERTAIN SUBSTITUTED 7-OXABICYCLO[2.2.1]2,5-HEPTADIENE METHANOLS

[75] Inventor: William A. Van Saun, Jr., Titusville, N.J.

[73] Assignee: FMC Corporation, Philadelphia, Pa.

[21] Appl. No.: 104,201

[22] Filed: Dec. 17, 1979

Related U.S. Application Data

[63] Continuation-in-part of Ser. No. 11,334, Feb. 12, 1979, abandoned.

[51] Int. Cl.$^3$ .................. A01N 45/12; C07D 307/00
[52] U.S. Cl. .................. 424/285; 260/346.2; 260/346.73
[58] Field of Search ............. 260/346.22, 346.73; 424/285

[56] References Cited
PUBLICATIONS

Synthetic Pyrethroids, ACS Symposium Series, No. 42, M. Elliot, Ed., Amer. Chem. Soc., Washington, D. C. 1977, Chapter 1.

*Primary Examiner*—Henry R. Jiles
*Assistant Examiner*—Bernard Dentz
*Attorney, Agent, or Firm*—Robert M. Kennedy; Robert L. Andersen; H. Robinson Ertelt

[57] ABSTRACT

Novel alcohols of the formula

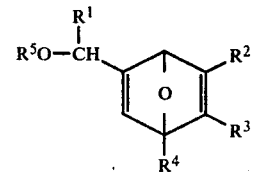

where $R^5$ is hydrogen are useful intermediates in the preparation of insecticidal esters. The insecticides are compounds in which $R^5$ is a substituted-vinylcyclopropanecarbonyl group, a tetramethylcyclopropanecarbonyl group, or a chlorophenyl-2-methylpropylcarbonyl group.

8 Claims, No Drawings

INSECTICIDAL ESTERS OF CERTAIN SUBSTITUTED 7-OXABICYCLO[2.2.1]2,5-HEPTADIENE METHANOLS

This application is a continuation-in-part of copending application U.S. Ser. No. 011,334, filed Feb. 12, 1979 now abandoned.

The present invention is directed to a novel alcohol for use in preparing cyclopropanecarboxylate and related insecticides, to insecticides employing this alcohol, and to an insecticidal method and composition. More particularly, the invention is directed to a 7-oxabicycloheptadienylmethanol and insecticidal esters thereof.

Pyrethins, naturally occurring extracts of chrysanthemum flowers, have long been of interest as insesticides. Since elucidation of the structures of these compounds, synthesis efforts have been directed toward preparation of related compounds having enhanced insecticidal activity and improved stability toward air and light. Since a prerequisite for insecticidal activity of pyrethroids is the presence in one molecule of an appropriate acid moiety and an appropriate alcohol moiety, research in the art has been directed toward novel acid and/or alcohol radicals. Noteworthy advances in the area of alcohol research were the discovery of 5-benzyl-3-furylmethyl alcohol, then of the more photostable 3-phenoxybenzyl alcohol (see *Synthetic Pyrethrodis,* ACS Symposium Series, No. 42, M. Elliott, Ed., American Chemical Society, Washington, D.C. 1977, Chapter 1). Similarly significant advances have been made in pyrethroid acid research. The commercial insecticide permethrin, the common name for 3-phenoxyphenyl-methyl 3-(2,2-dichloroethenyl)-2,2-dimethylcyclopropanecarboxylate, exemplifies use of both newer acid and alcohol moieties in a single compound.

The present invention provides a novel bicyclic alcohol and certain ester derivatives thereof which have a high level of insecticidal activity.

In this application, the term "lower" as applied to an aliphatic hydrocarbon group means having 1 to 6 carbon atoms, preferably 1 to 4 carbon atoms. The term "halo" or "halogen" means bromine, chlorine or fluorine. The term "haloalkyl" means an alkyl group of 1 to 3 carbon atoms substituted with 1 or more halogen atoms and includes perhaloalkyl of 1 to 3 carbon atoms. These definitions are applicable throughout the specification and claims except where a contrary meaning is clearly indicated.

The novel compounds of this invention have the general formula

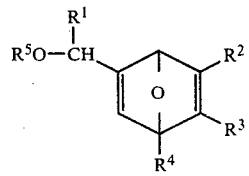

I wherein $R^1$ is a hydrogen atom, a cyano group, an ethynyl group, a haloalkyl group, an aminocarbonyl group, or an aminothioxomethyl group; $R^2$ and $R^3$, the same or different, are nitro, halogen, cyano, lower alkyloxycarbonyl, lower alkylsulfinyl, lower alkylsulfonyl, or the group $-CONR^6R^7$ or $-SO_2NR^6R^7$ where $R^6$ and $R^7$ are independently hydrogen, lower alkyl, or halo(lower)alkyl; $R^4$ is phenyl, benzyl, or benzoyl, optionally substituted with halogen or lower alkyl; $R^5$ is hydrogen, 2,2,3,3-tetramethylcyclopropylcarbonyl, 1-(4-chlorophenyl)-2-methylpropyl-1-carbonyl, or a cyclopropanecarboxylic acid residue of the formula:

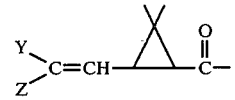

II wherein Y and Z, the same or different, are hydrogen, halogen, lower alkyl, haloalkyl, phenyl optionally substituted with halogen or lower alkyl, or phenylthio optionally substituted with halogen or lower alkyl. In formula I oxygen may be replaced with an atom of sulfur, an NR group where R is hydrogen or lower alkyl, or a methylene group as disclosed in the specification and claims of U.S. Ser. No. 011,334, the disclosure of which is incorporated herein by reference.

Particularly useful insecticides of the present invention are the cyclopropanecarboxylates in which one of Y and Z is halogen, such as chlorine or bromine, and the other, the same or different, is halogen or a haloalkyl group such as trihalomethyl, $R^1$ is hydrogen, $R^2$ and $R^3$ are each lower alkyloxycarbonyl, and $R^4$ is benzyl.

The cyclopropanecarboxylates having the acid residue of formula II have cis and trans isomeric forms, i.e., the carboxy and the substituted vinyl groups at the 1 and 3 positions of the cyclopropane ring are either cis or trans with respect to each other. Preparation of these compounds will usually yield a mixture of the cis and trans isomers, designated herein as cis,trans, in which the ratio of cis to trans may vary over a wide range. For purposes of this application the designations cis and trans are assigned in accordance with P. E. Burt, et al., *Pestic. Sci.,* 5 791–799 (1974). The compounds of this invention may also exist as E or Z isomers or as mixtures of E and Z isomers, designated E,Z, depending upon the spatial relationship of substituents on the $\alpha$-carbon of the vinyl group to those on the $\beta$-carbon of the vinyl group.

In the cyclopropanecarboxylate are it is known there may be substantial differences in the level of insecticidal activity of the cis and trans isomers. In general, as between the cis and trans isomer of a given cyclopropanecarboxylate, the cis isomer is usually more active than the trans and also more active than the cis,-trans mixture. Similar differences in activity may also occur with respect to the E and Z isomers.

Unless a contrary intent is specifically expressed, this invention embodies and includes both cis and trans isomeric forms of the claimed compounds as well as mixtures thereof wherein the cis to trans ratio is within the range of 0:100 to 100:0. Similarly, while the invention is illustrated with a mixture of the E and Z isomers, the individual isomers, as well as the mixtures, are contemplated by and within the scope of the invention. The various enantiomers of the claimed compounds and mixtures of them are also included within the scope of the invention.

The insecticidal compounds of this invention may be prepared in a number of ways. The schemata below for 2,3-bis(methoxycarbonyl)-4-phenylmethyl-7-oxabicyclo[2.2.1]hepta-2,4-diene-6-ylmethyl 3-(2,2-dichloroethenyl)2,2-dimethylcyclopropanecarboxylate is illustra-

ROUTE A:

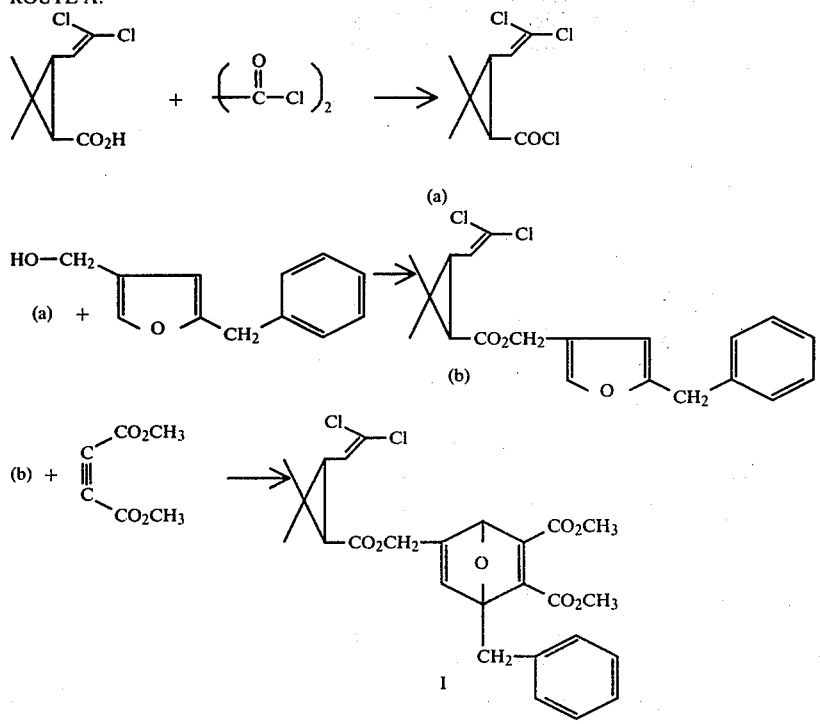

ROUTE B:

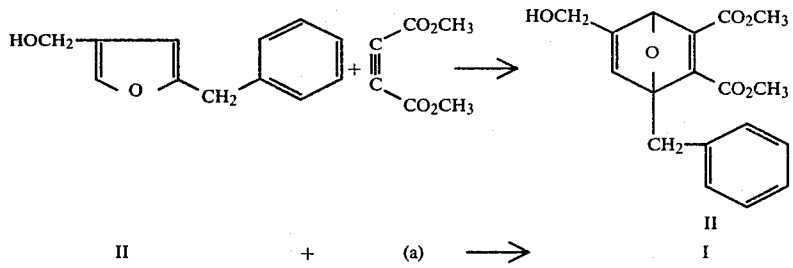

In Route A, an appropriate ester is converted via a cycloaddition reaction with an acetylenic compound to the novel ester I, the cycloaddition reaction and the point of novelty being the last step in the process. In Route B the cycloaddition of the acetylenic compound is to an appropriate alcohol to give the novel bicyclic alcohol II which is then converted by methods analogous to those known in the art to the novel ester I. In this latter route, novelty attaches in the first step of the process.

The Examples which follow illustrate preparation of the insecticidal compounds and novel intermediates therefor in accordance with the general methods described above. In the Examples, all temperatures are in degrees centigrade and all pressures in mm. Hg.

EXAMPLE 1

SYNTHESIS OF 2,3-BIS(METHOXYCARBONYL)-4-PHENYL-METHYL-7-OXABICYCLO[2.2.1]HEPTA-2,5-DIENE-6-YL-METHYL CIS-3-(2,2-DICHLOROETHENYL)-2,2-DIMETHYlCYCLOPRPANECARBOXYLATE

A. Synthesis of [5-(phenylmethyl)-3-furanyl]methyl cis-3-(2,2-dichloroethenyl)-2,2-dimethylcyclopropanecarboxylate as an intermediate Under a dry nitrogen atmosphere, a stirred solution of 6.3 grams (0.03 mole) of cis-3-(2,2-dichloroethenyl)-2,2-dimethylcyclopropanecarboxylic acid in 50 ml of dry toluene was heated to gentle reflux. Oxalyl chloride, 3.1 grams (0.03 mole), was added dropwise. When all of the oxalyl chloride had been added the solution was heated under reflux for an additional 10 minutes and then allowed to cool. This solution contained cis-3-(2,2-dichloroethenyl)-2,2-dimethylcyclopropanecarboxylic acid chloride.

Under a dry nitrogen atmosphere a solution was prepared by dissolving 5.7 grams (0.03 mole) of [5-(phenylmethyl)-3-furanyl]methanol and 5.2 grams (0.07 mole) of pyridine in 100 ml of dry toluene. The acid chloride solution above was added to this solution slowly with stirring. The resulting mixture was heated under reflux for one hour, then allowed to stand at ambient temperature for sixty hours.

The mixture was transferred to a separatory funnel along with water and diethyl ether rinsings. The aqueous phase was removed and the organic layer was washed, in succession, with three portions of water, one portion of aqueous 2% hydrochloric acid, one portion of water, one portion of aqueous 2% hydrochloric acid, two portions of water, two portions of aqueous 10% sodium carbonate, two portions of water, and finally, one portion of an aqueous saturated solution of sodium chloride. The organic layer was dried with anhydrous magnesium sulfate, filtered, and the solvent removed under reduced pressure to give 11.8 grams of [5-(phenylmethyl)-3-furanyl]methyl cis-3-(2,2-dichloroethenyl)-2,2-dimethylcyclopropanecarboxylate as a clear brown oil.

The nmr spectrum was consistent with the assigned structure.

B. Reaction of [5-(phenylmethyl)-3-furanyl]methyl cis-3-(2,2-dichloroethenyl)-2,2-dimethylcyclopropanecarboxylate with dimethyl acetylenedicarboxylate A stirred solution of 3.6 grams (0.01 mole) of [5-(phenylmethyl)-3-furanyl]methyl cis-3-(2,2-dichloroethenyl)-2,2-dimethylcyclopropanecarboxylate, prepared in step A above, and 1.4 grams (0.01 mole) of dimethyl acetylenedicarboxylate in 50 ml of toluene was heated under reflux for 6 hours. The reaction mixture was then allowed to stand at ambient temperature for 60 hours. The solvent was removed under reduced pressure to give 5.2 grams of crude product as a brown oil.

The brown oil was subjected to column chromatography using a column of silica gel. Elution was accomplished with a 50:50 hexane:methylene chloride mixture, then pure methylene chloride. The chromatographic procedure was repeated three times. The appropriate fractions were combined and concentrated under reduced pressure to give 2,3-bis(methoxycarbonyl)-4-phenylmethyl-7-oxabicyclo[2.2.1]hepta-2,5-diene-6-ylmethyl cis-3-(2,2-dichloroethenyl)-2,2-dimethylcyclopropanecarboxylate as an oil.

The nmr spectrum was consistent with the assigned structure.

Analysis calc'd for $C_{26}H_{26}Cl_2O_7$: C 59.89; H, 5.03; Found: C 59.84; H 5.00.

EXAMPLE 2

SYNTHESIS OF 2,3-BIS(METHOXYCARBONYL)-4-PHENYL-METHYL-7-OXABICYCLO[2.2.1]HEPTA-2,5-DIENE-6-YL-METHYL CIS-3-[2-(E,Z)-CHLORO-3,3,3-TRIFLUORO-PROPENYL]-2,2-DIMETHYLCYCLO-PROPANECARBOXYLATE

A. Synthesis of 2,3bis(methoxycarbonyl)-4-phenylmethyl-7-oxabicyclo[2.2.1]hepta-2,5-diene-6-methanol as an intermediate A stirred solution of 5.6 grams (0.03 mole) of [5-(phenylmethyl)-3-furanyl]methanol (phenylmethyl)-3-furanyl]methanol and 4.3 grams (0.03 mole) of dimethyl acetylenedicarboxylate in 100 ml of toluene was heated under reflux for 3 hours. The solvent was removed under reduced pressure to give approximately 10 grams of 2,3-bis(methoxycarbonyl)-4-phenylmethyl-7-oxabicyclo[2.2.1] hepta-2,5-diene-6-methanol. The alcohol was used without further purification.

B. Esterification of cis-3-[2-(E,Z)-chloro-3,3,3-trifluoropropenyl]-2,2-dimethylcycloprpanecarboxylic acid with 2,3-bis(methoxycarbonyl)-4-phenylmethyl-7-oxabicyclo[2.2.1]hepta-2,5-diene-6-methanol Under a dry nitrogen atmosphere, a stirred solution of 2.4 grams (0.01 mole) of cis-3-[2-(E,Z)-chloro-3,3,3trifluoropropenyl]-2,2-dimethylcyclopropanecarboxylic acid in 35 ml of dry toluene, was heated to gentle reflux and 1.3 grams (0.01 mole) of oxalyl chloride was cautiously added portionwise. Upon complete addition the reaction mixture was heated under reflux for an additional 10 minutes, then allowed to cool. This solution contained cis-3-[2-(E,Z)-chloro-3,3,3-trifluoropropenyl]-2,2-dimethylcyclopropanecarboxylic acid chloride.

Under a dry nitrogen atmosphere a solution was prepared by dissolving 3.3 grams (0.01 mole) of 2,3-bis-(methoxycarbonyl)-4-phenylmethyl-7oxabicyclo[2.2.1-]hepta-2,5-diene-6-methanol, prepared in step A above, and 1.6 grams (0.02 mole) of pyridine in 50 ml of dry toluene. The acid chloride solution from above was slowly added with stirring to this solution. Upon complete addition the reaction mixture was heated under reflux for two hours, then allowed to cool to ambient temperature and to stand for 60 hours. The reaction mixture was transferred to a separatory funnel along with water and diethyl ether rinsings. The aqueous layer was removed and the organic layer washed successively with three portions of water, one portion of aqueous 2% hydrochloric acid, one portion of water, one portion of aqueous 2% hydrochloric acid, two portions of water, two portions of aqueous 10% sodium carbonate, two portions of water and finally, one portion of an aqueous saturated solution of sodium chloride. The organic layer was dried with magnesium sulfate, filtered and the solvent removed under reduced pressure to give 5.5 grams of red residual oil. The oil was subjected to column chromatography using a column of silica gel. Elution was accomplished with methylene chloride. Appropriate fractions were combined and the solvent removed under reduced pressure to give 2.7 grams of residual oil which was subjected to further chromatography on silica gel. Elution was accomplished with 1:50 ethyl acetate:hexane. The appropriate fractions were combined, and concentrated under reduced pressure to give 2.4 grams of 2,3-bis(methoxycarbonyl)-4-phenylmethyl-7-oxabicyclo[2.2.1]-hepta-2,5-diene-6-ylmethyl cis-3-[2-(E,Z)-chloro-3,3,3-trifluoropropenyl)-2,2-dimethylcyclopropanecarboxylate. The nmr spectrum was consistent with the assigned structure.

Analysis calc'd for $C_{27}H_{26}ClF_3O_7$: C 58.43; H 4.72; Found: C 58.48; H 4.74.

In the method aspect of this invention, an effective insecticidal amount of the compound wherein $R^5$ is other than hydrogen is applied to the locus where insect control is desired, i.e., to the insect inself or to the foliage or seeds of agricultural plants. The compounds are useful for the control of household, veterinary, and crop insects and may be applied as technical material or as formulate product. Typical formulations include compositions of the active ingredient in combination with an agriculturally acceptable carrier or extender, preferably with a surface active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application. With due consideration to these factors the active ingredient of a typical formulation may, for example, be suitably present at a concentration of about 0.01% up to about 99.5%, preferably 0.1% up to 90%, of the formulation. An agriculturally acceptable carrier may comprise about 99.5% by weight to as low as about 0.5% by weight of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A concentration of the active ingredient in the use dilution may be in the range of 0.01% to about 10% by weight.

Many variations of spraying, dusting, and controlled or slow release compositions of a type known in the art may be used by substituting or adding a compound or compounds of this invention into the compositions known or apparent to the art.

The compounds of this invention may be formulated and applied with other compatible active agents including nematicides, insecticides, acaracides, fungicides, plant regulators, herbicides, fertilizers, and the like.

In applying these compounds, whether alone or with other agricultural chemicals, an effective insecticidal amount of the active ingredient must be applied. While the application rate will vary widely depending on the choice of compound, formulation, mode of application, plant species being protected, planting density and other like factors, a suitable use rate for agricultural crops may be in the range of 0.005 to 3 k/ha, preferably 0.01 to about 1 k/ha.

The compounds of this invention were tested for insecticidal activity as described below.

EXAMPLE 3

Initial Contact Activity: The test compound was dissolved in a small amount of acetone, and the acetone solution was dispersed in water containing one drop of isooctylphenyl polyethoxyethanol to give a solution having 512 ppm (w/w) active ingredient. An aliquot of this solution was diluted further with water to give a solution having 64 ppm (w/w) active ingredient. Test organisms and techniques were as follows: the activity against Mexican bean beetle (*Epilachna varivestis* Muls.) and southern armyworm (*Spodoptera eridania* [Cram.]) was evaluated by dipping the leaves of pinto bean plants into the test solution or spraying with the test solution and infesting the leaves with the appropriate immature form insects after the foliage had dried. The activity against the pea aphid (*Acyrthosiphon pisum* [Harris]) was evaluated on broad bean plants the leaves of which were dipped or sprayed before infestation with adult aphids. The activity against twospotted spider mites (*Tetranychus urticae* [Koch]) was evaluated on pinto bean plants the leaves of which were dipped or sprayed with test solution after infestation with adult mites. All organisms in the tests were maintained in a holding room at 80° F. and 50% relative humidity for an exposure period of at least 48 hours. At the end of this time the dead and living insects or mites were counted, and the percent kill was calculated. Results of these tests are summarized in Table I. Table I also reports data at 64 parts per million for the commercial insecticide permethrin, 3-phenoxyphenylmethyl (±) cis,trans-3-(2,2-dichloroethenyl)-2,2-dimethylcyclopropane-1-carboxylate. The claimed compounds in general exhibited excellent initial activity when compared with that of the reference compound. In the table the abbreviations MBB, SAW, PA, and SM are for Mexican bean beetle, southern armyworm, pea aphid, and twospotted spider mite respectively.

TABLE I

| | INITIAL ACTIVITY | | | | |
|---|---|---|---|---|---|
| | | Percent Kill | | | |
| Compound of Example | Conc. (ppm) | MBB | SAW | PA | SM |
| 1 | 512 | 100 | 100 | 100 | 0 |
| | 64 | 100 | 100 | 75 | 0 |
| 2 | 512 | 100 | 100 | 95 | 0 |
| | 64 | 100 | 100 | 85 | 0 |
| permethrin | 64 | 100 | 100 | 80 | 0 |

EXAMPLE 4

Topical Application Test:

The compounds of this invention were tested for insecticidal activity by applying to the insect appropriate amounts of a toxicant solution containing 5 mg/l of toxicant in acetone. The tests were read twenty-four hours after application of the toxicant solution and the percent kill determined. The well known commercial insecticide permethrin, 3-phenoxyphenylmethyl (±) cis-trans-3-(2,2-dichloroethenyl)-2,2-dimethylcyclopropanecarboxylate, was used as the standard for comparison. Relative potency, based on a value of 1.0 for permethrin was determined by comparing the $LD_{50}$ for the test compound with that for the standard. The insects employed were southern armyworm (*Spodoptera eridania*), cabbage looper (*Trichoplusia ni* [Hubner]), beet armyworm (*Spodoptera exigua* [Hubner]), Mexican bean beetle (*Epilachna varivestis* Muls.) and milkweed bug (*Oncopeltus faciatus* [Dallas]). The results, shown in Table II, indicate a high order of insecticidal activity for the claimed compounds. With the exception of compound 1 against the cabbage looper and Mexican bean beetle, the claimed compounds exhibited substantially higher levels of activity than permethrin. In the table the abbreviations SAW, CL, BAW, MBB, and MWB are for southern armyworm, cabbage looper, beet armyworm, Mexican bean beetle and milkweed bug respectively.

TABLE II

| | Topical Application Test | | | | |
|---|---|---|---|---|---|
| Compound of Example | Relative Potency | | | | |
| | SAW | CL | BAW | MBB | MWB |
| permethrin | 1.0 | 1.0 | 1.0 | 1.0 | 1.0 |
| 1 | 2.3 | 0.6 | 2.3 | 1.0 | 9.0 |
| 2 | 2.9 | 1.8 | 7.1 | 3.7 | — |

I claim:

1. A compound of the formula

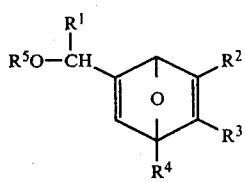

wherein $R^1$ is hydrogen, an ethynyl group, a cyano group, a haloalkyl group, an aminocarbonyl group, or an aminothioxomethyl group; $R^2$ and $R^3$, the same or different, are nitro, halogen, cyano, lower alkyloxycarbonyl, lower alkylsulfinyl, lower alkylsulfonyl, or the group —$CONR^6R^7$ or —$SO_2NR^6R^7$ where $R^6$ and $R^7$ are independently hydrogen, lower alkyl, or halo(lower)alkyl; $R^4$ is phenyl, benzyl or benzoyl, optionally substituted with halogen or lower alkyl; $R^5$ is 2,2,3,3-tetramethylcyclopropylcarbonyl, 1-(4-chlorophenyl)-2-methylpropyl-1-carbonyl, or a cyclopropanecarboxylic acid residue of the formula

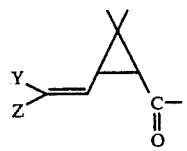

wherein Y and Z, the same or different, are hydrogen, halogen, lower alkyl, haloalkyl, phenyl optionally substituted with halogen or lower alkyl, or phenylthio optionally substituted with halogen or lower alkyl.

2. The compound of claim 1 wherein $R^5$ is a cyclopropanecarboxylic acid residue of the formula:

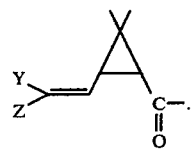

3. The compound of claim 2 wherein one of Y and Z is halogen and the other is halogen or trihalomethyl.

4. The compound of claim 3 wherein $R^2$ and $R^3$ are lower alkoxycarbonyl and $R^4$ is benzyl.

5. The compound of claim 4 wherein $R^1$ is hydrogen, and $R^2$ and $R^3$ are each methoxycarbonyl.

6. An insecticidal composition comprising an insecticidally effective amount of the compound of claims 1, 2, 3, 4, or 5 in admixture with a compatible extender or carrier.

7. A method for controlling insects which comprises applying to the insect or to a locus where control is desired an insecticidally effective amount of the compound of claims 1, 2, 3, 4, or 5.

8. A method for controlling insects which comprises applying to the insect or to a locus where control is desired an insecticidally effective amount of the composition of claim 6.